United States Patent
Ohtani et al.

(10) Patent No.: US 10,342,785 B2
(45) Date of Patent: Jul. 9, 2019

(54) USE OF EP4 RECEPTOR ANTAGONISTS FOR THE TREATMENT OF NASH-ASSOCIATED LIVER CANCER

(71) Applicant: AskAt Inc., Aichi (JP)

(72) Inventors: Naoko Ohtani, Tokyo (JP); Fumitaka Kamachi, Tokyo (JP); Tze Mun Loo, Tokyo (JP); Shinichi Koizumi, Aichi (JP); Takako Okumura, Aichi (JP)

(73) Assignee: AskAt Inc., Aichi (JP)

( * ) Notice: Subject to any disclaimer, the term of this patent is extended or adjusted under 35 U.S.C. 154(b) by 3 days.

(21) Appl. No.: 15/343,999

(22) Filed: Nov. 4, 2016

(65) Prior Publication Data

US 2018/0125832 A1    May 10, 2018

(51) Int. Cl.
| | |
|---|---|
| *A61K 31/4412* | (2006.01) |
| *A61P 35/00* | (2006.01) |
| *A61K 31/192* | (2006.01) |
| *A61K 31/44* | (2006.01) |
| *A61K 45/06* | (2006.01) |
| *A61K 31/64* | (2006.01) |

(52) U.S. Cl.
CPC ........ *A61K 31/4412* (2013.01); *A61K 31/192* (2013.01); *A61K 31/44* (2013.01); *A61K 31/64* (2013.01); *A61K 45/06* (2013.01); *A61P 35/00* (2018.01)

(58) Field of Classification Search
None
See application file for complete search history.

(56) References Cited

U.S. PATENT DOCUMENTS

| | | |
|---|---|---|
| 6,710,054 B2 | 3/2004 | Nakao et al. |
| 6,710,205 B2 | 3/2004 | Tani et al. |
| 6,861,441 B1 | 3/2005 | Clayton et al. |
| 7,141,580 B2 | 11/2006 | Nakao et al. |
| 7,196,198 B2 | 3/2007 | Tani et al. |
| 7,238,714 B2 | 7/2007 | Nakao et al. |
| 7,479,564 B2 | 1/2009 | Nakao et al. |
| 7,534,914 B2 | 5/2009 | Koike et al. |
| 8,921,391 B2 | 12/2014 | Take et al. |
| 2002/0107273 A1 | 8/2002 | Nakao et al. |
| 2003/0114435 A1 | 6/2003 | Tani et al. |
| 2003/0220372 A1 | 11/2003 | Hirano et al. |
| 2004/0127487 A1 | 7/2004 | Tani et al. |
| 2004/0181059 A1 | 9/2004 | Nakao et al. |
| 2005/0065188 A1 | 3/2005 | Nakao et al. |
| 2005/0250818 A1 | 11/2005 | Koike et al. |
| 2005/0267170 A1 | 12/2005 | Koike et al. |
| 2007/0155732 A1 | 7/2007 | Nakao et al. |
| 2009/0018158 A1 | 1/2009 | Haruta et al. |
| 2009/0099226 A1 | 4/2009 | Belley et al. |
| 2009/0163558 A1 | 6/2009 | Koike et al. |
| 2015/0004175 A1 | 1/2015 | Kaech et al. |
| 2015/0190506 A1* | 7/2015 | Cheung |

FOREIGN PATENT DOCUMENTS

| | | |
|---|---|---|
| EP | 2422779 A1 * | 2/2012 |
| JP | 2004-517054 | 6/2004 |
| JP | 2007-504210 | 3/2007 |
| JP | 2007-536366 | 12/2007 |
| JP | 2007-536367 | 12/2007 |
| JP | 2008-540584 | 11/2008 |
| WO | 01/10426 | 2/2001 |
| WO | 01/62708 | 8/2001 |
| WO | 02/32900 | 4/2002 |
| WO | 03/086390 | 10/2003 |
| WO | 03/086391 | 10/2003 |
| WO | 2005/021508 | 3/2005 |
| WO | 2005/102389 | 11/2005 |
| WO | 2005/105732 | 11/2005 |
| WO | 2006/095268 | 9/2006 |
| WO | 2013/040316 | 3/2013 |
| WO | 2015/179615 | 11/2015 |

OTHER PUBLICATIONS

Truong et al., "Metastatic Hepatocellular Carcinoma Responsive to Pembrolizumab", Cureus, Jun. 2016, vol. 8(6): e631, 4 pages.*
Torres et al., "Nonalcoholic Steatohepatitis and Noncirrhotic Hepatocellular Carcinoma", Fertile soil, Semin Liver Dis, 2012, vol. 32, pp. 30-38.
Bhaskaran et al., "Body-mass index and risk of 22 specific cancers: a population-based cohort study of 5.24 million UK adults", Lancet, vol. 384, pp. 755-765, (2014).
Calle et al., "Overweight, Obesity, and Mortality from Cancer in a Prospectively Studied Cohort of U.S. Adults", N. Engl. J. Med., vol. 348, No. 17, pp. 1625-1638, (Apr. 24, 2003).
Calle et al., "Overweight, Obesity and Cancer: Epidemiological Evidence and Proposed Mechanisms", Nature Reviews Cancer, vol. 4, pp. 579-591, (Aug. 2004).
Chen et al., "Prostaglandin E2 and programmed cell death 1 signaling coordinately impair CTL function and survival during chronic viral infection", Nat. Med., 2015, vol. 21, pp. 327-334.
El-Serag, H. B, "Hepatocellular Carcinoma", N Engl J Med, vol. 365, issue 12, pp. 1118-1127, (2011).
Konya V. et al., "E-type prostanoid receptor 4 (EP4) in disease and therapy", Pharmacology & Therapeutics, 2013, vol. 138, pp. 485-502.
Marengo, A. et al., "Liver Cancer: Connections with Obesity, Fatty Liver, and Cirrhosis", Annu. Rev. Med., vol. 67, pp. 103-117 (2016), Abstract only.
Michelotti et al., "NAFLD, NASH and liver cancer", Nat. Rev. Gastroenterol Hepatol, vol. 10, pp. 656-665 (2016).
Streba, L. A. et al., "Nonalcoholic fatty liver disease, metabolic risk factors, and hepatocellular carcinoma: An open question", World Journal of Gastroenterology, vol. 21, issue 14, pp. 4103-4110 (Apr. 14, 2015).

(Continued)

*Primary Examiner* — Savitha M Rao
*Assistant Examiner* — Gregg Polansky
(74) *Attorney, Agent, or Firm* — Wenderoth, Lind & Ponack, L.L.P.

(57) ABSTRACT

This invention is directed to prostaglandin E2 receptor 4 (EP4) antagonists useful in the treatment of nonalcoholic steatohepatitis (NASH)-associated liver cancer in a human or animal. The method comprises administering one or more of Compound A, Compound B or Compound C, or pharmaceutically acceptable salts thereof, as the EP4 antagonist(s). The method may include a pharmaceutical composition comprising the EP4 antagonist, and may include one or more other active agents and/or therapies.

24 Claims, 9 Drawing Sheets

(56) References Cited

OTHER PUBLICATIONS

Xia S et al., "Prostaglandin E2 promotes the cell growth and invasive ability of hepatocellular carcinoma cells by upregulating c-myc expression via EP4 receptor and the PKA signaling pathway", Oncology Reports, 2014, vol. 32, pp. 1521-1530.

Xu Y et al., "Activated hepatic stellate cells promote liver cancer by induction of myeloid-derived suppressor cells through cyclooxygenase-2", Oncotarget, 2016, vol. 7, No. 8, pp. 8866-8878.

Yokoyama et al., "The Prostanoid EP4 Receptor and Its Signaling Pathway"., Pharmacol. Rev., 2013, vol. 65, pp. 1010-1052.

X. Ma et al., "Prostaglandin E Receptor EP4 Antagonism Inhibits Breast Cancer Metastasis", Cancer Research, vol. 66, No. 6, pp. 2923-2927, 2006.

D. P. Cherukuri et al., "The EP4 Receptor antagonist, L-161,982, Blocks Prostaglandin $E_2$-Induced Signal Transduction and Cell Proliferation in HCA-7 Colon Cancer Cells", Experimental Cell Research, vol. 313, No. 14, pp. 2969-2979, 2007.

T. Kitamura et al., "Combined Effects of Prostaglandin E Receptor Subtype $EP_1$, and Subtype EP4 Antagonists on Intestinal Tumorigenesis in *Adenomatous Polyposis coli* Gene Knockour Mice", Cancer Science, vol. 94, No. 7, pp. 618-621, Jul. 2003.

Yang et al., "Host and Direct Antitumor Effect and Profound Reduction in Tumor Metastasis with Selective EP4 Receptor Antagonism", Cancer Research, vol. 66, No. 19, Oct. 1, 2006, pp. 9665-9672.

Murase et al., "Characterization of Binding Affinity of CJ-023,423 for Human Prostanoid $EP_4$ Receptor", Pharmacology, vol. 82, No. 1, 2008, pp. 10-14.

J. G. Cannon, Chapter Nineteen in Burger's Medicinal Chemistry and Drug Discovery, Fifth Edition, vol. I: Principles and Practice, Wiley-Interscience 1995, pp. 783-802, 784.

Wu et al. "A human colonic commensal promotes colon tumorigenesis via activation of T helper type 17 T cell responses", Nature Medicine, Sep. 2009, vol. 15, No. 9, pp. 1016-1023.

Sinha et al. "Prostaglandin E2 Promotes Tumor Progression by Inducing Myeloid-Derived Suppressor Cells", Cancer Res, May 2007, vol. 67, No. 9, pp. 4507-4513.

Sheridan, R.P. "The Most Common Chemical Replacements in Drug-Like Compounds", J. Chem. Inf. Comput. Science, 2002, vol. 42, pp. 103-108.

Wang et al. "Prostaglandin E2 induces Vascular Endothelial Growth Factor Secretion in Prostrate Cancer Cells Through EP2 Receptor-Mediated cAMP Pathway", Molecular Carcinogenesis, 2007, vol. 46, pp. 912-923.

Han et al. "Suppression of prostaglandin E-2 receptor subtype EP2 by PPARgamma ligands inhibits human lung carcinoma cell growth", Biochemical and Biophysical Research Communications, 2004, vol. 314, pp. 1093-1099.

Chell et al. "Increased EP4 Receptor Expression and Colorectal Carcinogenesis Progression Promotes Cell Growth and Anchorage Independence", Cancer Research, 2006, vol. 66, No. 6, pp. 3106-3113.

Timoshenko et al. "Role of prostaglandin $E_2$ receptors in migration of murine and human breast cancer cells" Experimental Cell Research, 2003, vol. 289, pp. 265-274.

Akio Murase et al., "In vitro pharmacological characterization of CJ-042794, a novel, potent, and selective prostaglandin EP4 receptor antagonist", Life Sciences, Jan. 16, 2008, vol. 82, No. 3-4, pp. 226-232.

Koji Takeuchi et al., "Effect of (S)-4-(1-(5-Chloro-2-(4-flurophenyoxy)benzamido)ethyl) Benzoic Acid (CJ-42794), a Selective Antagonist of Prostaglandin E Receptor Subtype 4, on Ulcerogenic and Healing Responses in Rat Gastrointestinal Mucosa", The Journal of Pharmacology and Experimental Therapeutics, Sep. 1, 2007, vol. 322, No. 3, pp. 903-912.

Sung et al., "Lack of Expression of the EP2 but not EP3 Receptor for Prostaglandin E2 Results in Suppression of Skin Tumor Development", Cancer Res, 2005, vol. 65, No. 20, pp. 9304-9311.

Ma et al., "A prostaglandin E (PGE) receptor EP4 antagonist protects natural killer cells from $PGE_2$-mediated immunosuppression and inhibits breast cancer metastasis", Oncoimmunology, 2013, 2, e22647.

Ohtani et al., "Obesity and Cancer: A Gut Microbial Connection", Cancer Research, vol. 74, issue 7, pp. 1885-1889, Apr. 1, 2014.

Fuertes et al., "Host type I IFN signals are required for antitumor $CD8^+$ T cell responses through $CD8\alpha^+$ dendritic cells", J. of Exp. Med., vol. 208, No. 10, pp. 2005-2016, Sep. 19, 2011.

Zelenay et al., "Cyclooxygenase-Dependent Tumor Growth through Evasion of Immunity", Cell, vol. 162, pp. 1257-1270, Sep. 10, 2015.

Yoshimoto et al., "Obesity-induces gut microbial metabolite promotes liver cancer through senescence secretome", Nature, 2013, vol. 499, pp. 97-101, Abstract.

Salmon et al., "Expansion and Activation of CD103(+) Dendritic Cell Progenitors at the Tumor Site Enhances Tumor Responses to Therapeutic PD-L1 and BRAF Inhibition", Immunity, 2016, vol. 44, pp. 924-938, Abstract.

International Search Report and Written Opinion of the International Searching Authority, dated Jan. 30, 2018 in corresponding International Patent Application No. PCT/JP2017/039680.

Okumura et al., "Discovery of AAT-008, a novel, potent, and selective prostaglandin EP4 receptor antagonist", Bioorganic & Medicinal Chemistry Letters, vol. 27: pp. 1186-1192 (2017).

Salmon et al., "Expansion and Activation of CD103(+) Dendritic Cell Progenitors at the Tumor Site Enhances Tumor Responses to Therapeutic PD-L1 and BRAF Inhibition", Immunity, 2016, vol. 44, pp. 924-938.

* cited by examiner

Vehicle; n=4

Compound A; n=5

Vehicle; n=4

Compound A; n=5

Vehicle; n=4

Compound A; n=5

Vehicle; n=4

Compound A; n=5

USE OF EP4 RECEPTOR ANTAGONISTS FOR THE TREATMENT OF NASH-ASSOCIATED LIVER CANCER

TECHNICAL FIELD

This invention relates to a prostaglandin E2 receptor 4 (EP4) antagonist for use in the treatment of nonalcoholic steatohepatitis (NASH)-associated liver cancer. The method for treatment of NASH-associated liver cancer comprises administering any one of Compound A, Compound B or Compound C, or a pharmaceutically acceptable salt thereof, as the EP4 antagonist (hereinafter, "the compounds of the invention"), or a pharmaceutical composition comprising the compounds of the invention to a human or animal. The method of treatment includes administering the compounds of the invention alone or in combination with one or more other active agents and/or therapies to the human or animal having the NASH-associated liver cancer. The method of treatment also includes a therapy which regulates specific immune cell functions and/or their distributions in tumor tissue of NASH-associated liver cancer by EP4 antagonists, including the compounds of the invention. Further, this invention relates to a pharmaceutical composition or a kit comprising the compounds of the invention or pharmaceutically acceptable salts thereof. Hereinafter, the "compounds of the invention" include any one of Compound A, Compound B and Compound C each alone or in combination, or a pharmaceutically acceptable salt of any one of these compounds.

BACKGROUND ART

Nonalcoholic fatty liver disease (NAFLD) is the most common cause of chronic liver disease in the United States with an estimated prevalence of 30 to 40% of the adult population. Although only 5 to 20% of NAFLD patients are generally considered to meet histopathologic criteria for nonalcoholic steatohepatitis (NASH), this still translates into a nationwide prevalence of 2 to 5% of the population who are at an increased risk of progression to cirrhosis. Cirrhosis itself is a sufficien risk factor for liver cancer including hepatocellular carcinoma (HCC). Obesity also appears to contribute to the risk of developing HCC with a meta-analysis of cohort studies showing a 90% increased risk of HCC in the obese. This may partially explain the growing rates of HCC in developed countries and the 80% increase in the annual incidence of HCC in the U.S. over the last two decades (Torres et al., Semin Liver Dis., 2012, 32(1):30-38).

Even more alarming is the fact that HCC has been shown to occur in patients having noncirrhotic NASH. Cumulatively, this data provides strong evidence that HCC can occur more in noncirrhotic NASH patients than in cirrhotic NASH patients, although larger prospective studies are required to obtain incidence rates. The connection between NASH and liver cancer has been well established. Large case studies have demonstrated a specific phenotype of older, predominantly male patients with coexisting metabolic syndrome that can develop HCC without a background of cirrhosis. Some of the purported complex pathophysiologic mechanisms that lead to this have been described, but a total understanding of the interplay and overlap between NASH promoting and oncogenic processes is still in development (Torres et al., Semin Liver Dis., 2012, 32(1):30-38).

Major causes of hepatitis and HCC can be divided into the following two categories: (1) infections with hepatitis B (HBV) and C viruses (HCV), and (2) metabolic causes, such as alcohol consumption and NAFLD. Generally, chronic viral infection-mediated hepatitis is the most common cause of hepatitis, followed by alcoholic liver diseases and NAFLD. Drug therapy of viral infection-mediated hepatitis is already established and the anti-viral therapy using interferon alpha and nucleotide analogs is commonly prescribed. On the other hand, drug therapy of NAFLD, NASH and diseases associated with liver cancer have not been established since the disease itself was only recently recognized.

Obesity has become a worldwide health problem and is known to increase the risk of diabetes, cardiovascular diseases, and several types of cancer. Among obesity-associated cancers, liver cancer has been shown to have a strong relationship with obesity, based on epidemiological studies (Bhaskaran et al., Lancet, 2014, 384: 755-765; Calle and Kaaks, Nature Reviews Cancer, 2004, 4:579-591; and Calle et al., New England J. Med., 2003, 348(17):1625-1638). The most common risk factor for HCC is long-term infection by HBV or HCV (El-Serag, New England J. Med., 2011, 365:1118-1127; and Marengo et al., Annual Review of Medicine, 2016, 67:103-117). However, obesity-associated NAFLD and NASH have recently emerged as risk factors for liver cancer (Marengo et al., Annual Review of Medicine, 2016, 67:103-117; Michelotti et al., Nat. Rev. Gastroenterol. Hepatol., 2013, 10:656-665; and Streba et al., World J. Gastroenterology, 2015, 21(14):4103-4110). There is no available therapeutic for NAFLD, NASH and NASH-associated liver cancer at present. Therefore, there is an urgent need for the development of a therapeutic for NASH-associated liver cancer.

Prostaglandins are mediators of pain, fever and other symptoms associated with inflammation. Prostaglandin E2 (PGE2) is the predominant eicosanoid expressed in inflammation conditions. PGE2 is also involved in various physiological and/or pathological conditions, such as hyperalgesia, uterine contraction, digestive peristalsis, awakeness, suppression of gastric acid secretion, blood pressure, platelet function, bone metabolism, angiogenesis, and cancer cell growth, invasion and metastasis, or the like. Non-patent references disclose the character of the prostanoid receptors, relationship with therapy, and selective agonists and antagonists most generally used (see, for example, Konya et al., Pharmacology & Therapeutics, 2013, 138:485-502; and Yokoyama et al., Pharmacol. Rev., 2013, 65:1010-1052).

PGE2 has been reported to be highly expressed in cancer tissues of various types of cancer, and it has also been demonstrated that PGE2 correlates to the initiation, growth and development of cancer and disease conditions of patients. It is generally accepted that PGE2 relates to activation of cell proliferation and cell death (apoptosis) and plays an important role in the processes of cancer cell proliferation, disease progression and cancer metastasis (see, for example, Konya et al., Pharmacology & Therapeutics, 2013, 138:485-502; and Yokoyama et al., Pharmacol. Rev., 2013, 65:1010-1052).

There are four PGE2 receptor subtypes, EP1, EP2, EP3 and EP4, which display different pharmacological properties. The EP4 receptor subtype belongs to the G protein-coupled receptor subfamily, known as a receptor with seven transmemblene domains. Accordingly, EP4 plays a significant role in biological events by stimulating cAMP signal-mediated functions. From the aspect of pharmacological studies, several investigations of compounds with EP4 receptor antagonistic activities have been conducted and EP4 receptor-selective antagonists are known (Konya et al., Pharmacology & Therapeutics, 2013, 138:485-502).

Regarding the role of the EP4 receptor in cancer, several non-patent references (e.g., Yokoyama et al., Pharmacol. Rev., 2013, 65:1010-1052; Ma et al., Oncolmmunology, 2013, 2(1):e22647) and patent literature (U.S. Pat. No. 8,921,391 B2) demonstrate the growth inhibitions and/or metastasis of the colon, breast, gastric, lung, prostate, and other cancer types in animal tumor models using EP4 receptor antagonists. Some patent literature (e.g., WO 2015/179615 A1 and US 2015/0004175 A1) shows therapeutic efficacy of an EP4 receptor antagonist or inhibition of EP4 signaling results in the inhibition of tumor growth. Moreover, EP4 signal inhibition in combination with other anticancer therapeutics or radiation therapy show additional benefits compared to each monotherapy (see WO 2015/179615 A1).

The role of the EP4 receptor in liver cancer has recently been reported in non-patent literature. PGE2/EP4 receptor signaling through PKA/CREB activation upregulated c-Myc expression and resulted in promoting cell growth in HCC cells in vitro (Xia et al., Oncology Reports, 2014, 32:1521-1530). PGE2 also promoted a hepatic stellate cell-induced myeloid-derived suppressor cell (MDSC) accumulation in in vitro and in vivo experiments which was supposed to stimulate growth of liver cancer (Xu et al., Oncotarget, 2016, 7(8):8866-8878). This literature indicated that PGE2/EP4 signaling may have some role in liver cancer growth. However, these references do not demonstrate liver cancer suppression of PGE2/EP4 signal inhibition in animals. Suppression of PGE2/EP4 receptor signaling alone (or in combination with a PD-1 antibody) restores $CD8^+$ T cell (CTL) functional activity (Chen et al., Nature Medicine, 2015, 21(4):327-334; and US 2015/0004175 A1). These references demonstrate that EP4 signal inhibition mediates activation of a host's CTL activity, but there is no direct evidence that EP4 signal inhibition or EP4 antagonistic activity has efficacy on HCC growth and/or metastasis.

U.S. Pat. No. 8,921,391 B2 demonstrates anti-tumor efficacies of Compound A, B, and/or C in gastric, lung, prostate, and other cancer types in animal tumor models. In this patent, liver cancer is noted as one of the cancer types in a one-word description without any experimental example, and liver cancer does not appear in any claim. Additionally, this patent does not disclose the treatment of "nonalcoholic steatohepatitis (NASH)-associated" liver cancer, and does not disclose any information relating to NASH or NAFLD.

In 2015, a critical concern of PGE2/EP4 signal inhibition in liver cancer therapy, especially in chronic virus-infection related diseases, such as HBV and HCV-mediated liver diseases, was reported. Inhibiting PGE2/EP4 signal causes significant induction or activation of PD-1 expression in virus-specific $CD8^+$ T cells (CTLs) in an animal model (Chen et al., Nature Medicine, 2015, 21(4):327-334). Increase of PD-1 expression on CTLs strongly suggests a suppression of key immunological function mediated by T cells against viral infection. In the case of chronically HBV- or HCV-infected liver cancers, the increase of PD-1 expression on CTLs should therefore cause a stimulation of viral expansion and also tumor development and growth. The impact of the increase of PD-1 expression on CTLs in tumor growth and development has been clearly demonstrated by the striking efficacy of their inhibitor (e.g., an anti-PD-1 antibody or an immune checkpoint inhibitor) in recent clinical cancer therapy. Accordingly, this research created a general concern for the risk of increasing tumor growth by PGE2/EP4 signal inhibition in the treatment of liver cancer. Thus, PGE2/EP4 signal inhibition was expected to activate PD-1 expression, which would suppress the immunological response against a viral infection, and then promote virus development and liver cancer development.

In view of this negative concern for EP4 signal inhibition in liver cancer therapy, the present inventors have unexpectedly found significant anti-tumor effects and suppression of PD-1 expression on $CD8^+$ T cells (CTLs) in NASH-associated liver cancer. This is contrary to the results on PD-1 expression in a virus-associated liver cancer model for an EP4 antagonist in monotherapy and in combination with another drug in an animal model. NASH-associated liver cancer has different causes from virus infection-associated liver cancer. To date, there is no evidence to support the EP4 mechanism, including EP4 antagonistic activity, in a therapy to treat NASH-associated liver cancer. Moreover, no evidence has been disclosed in the art relating to the efficacy of a combination therapy of the EP4 receptor with any other therapies in the treatment of NASH-associated liver cancer. Accordingly, the use of an EP4 antagonist on NASH-associated liver cancer is unexpected over the art.

SUMMARY OF INVENTION

Technical Problem

As discussed above, obesity has become a worldwide health problem and is known to increase the risk of several types of cancer. Obesity-associated liver cancer has causative risk factors different from that of HCC mediated by long-term infection by HBV or HCV. Liver cancer has been shown to have a strong relationship with obesity, based on epidemiological studies. Further, obesity-associated NAFLD and NASH have recently emerged as risk factors for liver cancer. As a result, the precise molecular mechanisms mediating the development of obesity- and/or NASH-associated liver cancer as well as therapeutics for these diseases are urgently needed. The treatment of chronic HBV- and HCV-infected liver cancer by PGE2/EP4 signal inhibition was expected to increase the liver cancer diagnosis by increasing PD-1 expression on CTL. As a result, there was concern for treating liver cancers, not only chronic virus infected liver cancer but also the alcoholic, NAFLD, and NASH-associated liver cancer with EP4 signal inhibition.

Solution to the Problem

The purpose of this invention is to provide a method for the treatment of NASH-associated liver cancer using an EP4 receptor antagonist either alone or in combination with available therapeutics. In achieving this goal, the present inventors have discovered that each of the following three compounds and pharmaceutically acceptable salts thereof, dramatically decrease the growth and development of obesity-induced NASH-associated liver cancer in a validated mouse model:

4-[(1S)-1-({[5-chloro-2-(3-fluorophenoxy)pyridin-3-yl] carbonyl}amino)ethyl]-benzoic acid (Compound A), 4-((1S)-1-{[5-chloro-2-(4-fluorophenoxy)benzoyl] amino}ethyl)benzoic acid (Compound B), and 3-[2-(4-{2-ethyl-4,6-dimethyl-1H-imidazo[4,5-c]pyridin-1-yl}phenyl)ethyl]-1-[(4-methylbenzene)sulfonyl]urea (Compound C).

Accordingly, the present invention is based on the discovery that the compounds of the invention have EP4-selective antagonistic activity and inhibited the growth and development of obesity-induced NASH-associated liver cancer in a mouse model. This is the first discovery in the world that an EP4 antagonist has therapeutic efficacy against obesity-induced NASH-associated liver cancer. Moreover, the inventors discovered that the treatment of the NASH-associated liver cancer with an EP4 antagonist in combination with a PD-1 antibody shows a synergistic effect of higher efficacy compared to the treatment with monotherapy of each drug.

Effect of the Invention

Therefore, the compounds of the invention are useful for patients who are required to receive treatment of NASH-associated liver cancer.

BRIEF EXPLANATION OF THE DRAWINGS

EP4 antagonist Compound A inhibits liver tumor development in an obesity-induced NASH-associated mouse liver cancer model (Ohtani et al., Cancer Research, 2014, 74:1885-1889).

The frequencies of CD11c$^{hi}$ MHC class II$^{hi}$ dendritic cells (DCs) and CD11b$^+$ DCs were not changed by the treatment of Compound A. The population of CD103 DCs, essential DCs for anticancer immune responses, was increased in the Compound A-treated group.

Figure 6A:
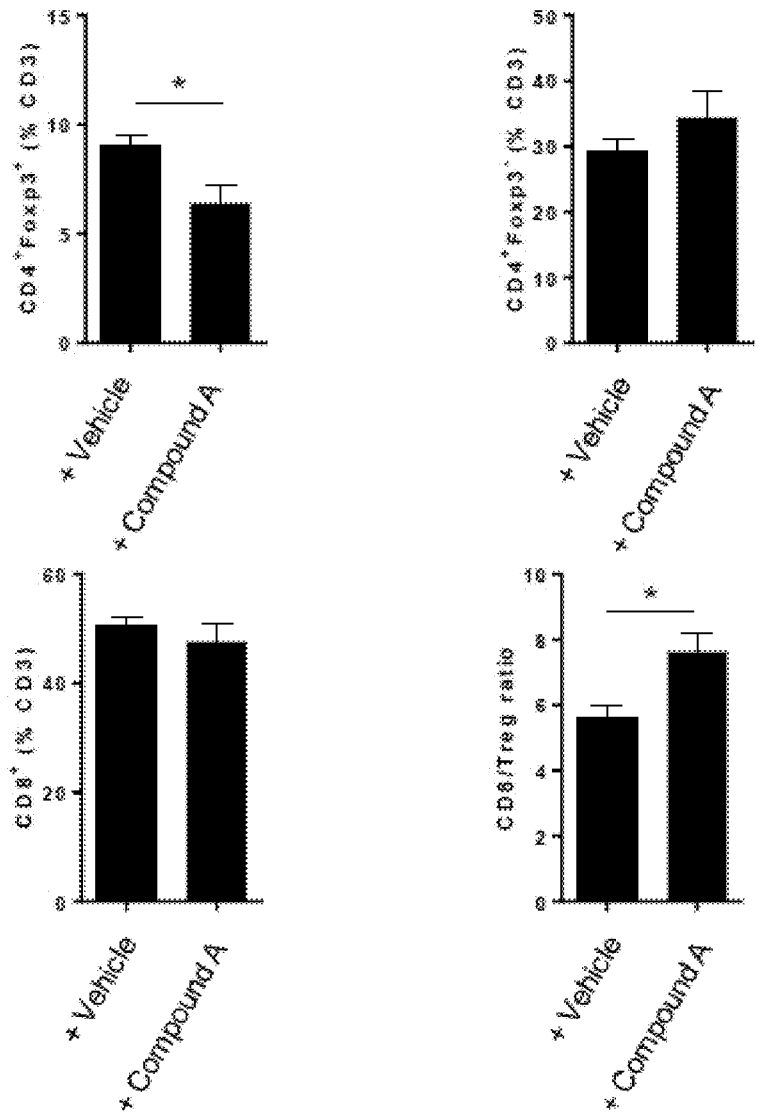

FIG. 6A depicts the percentages of CD3$^+$ CD4$^+$ Foxp3$^+$, CD3$^+$ CD4$^+$ Foxp3$^-$, CD3$^+$ CD8$^+$ cells analyzed by flow cytometry. The ratio of CD8$^+$ T cells to CD4$^+$ Foxp3$^+$ Tregs was calculated. Data are represented as means±SEM. NS=not significant, *p<0.05, *p<0.01.

Figure 6B:
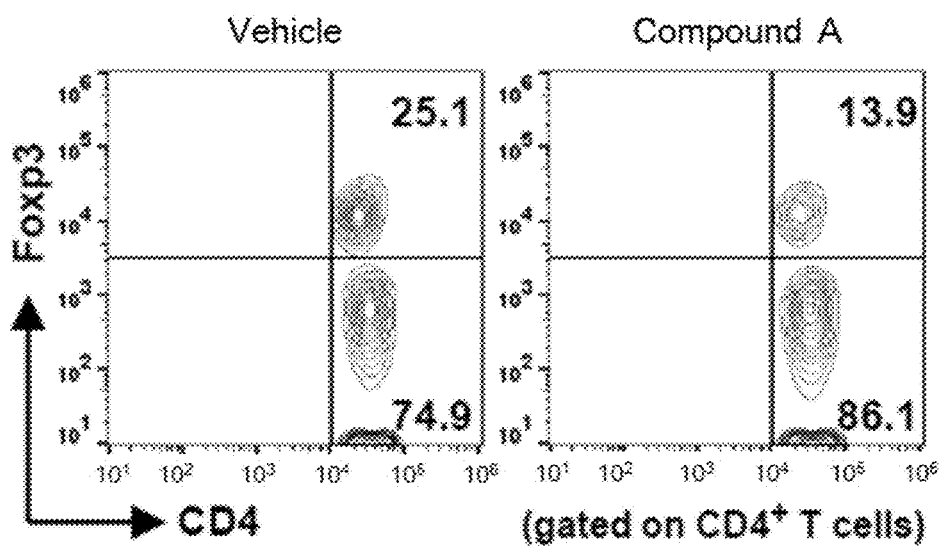

FIG. 6B depicts dot plots of Foxp3 expression in CD4$^+$ T cell compartments of livers from vehicle-treated mice (left side) and Compound A-treated mice (right side). The numbers in the plots indicate the percentages of cells in the indicated gate. The frequency of CD4$^+$Foxp3$^+$ regulatory T cells (Tregs), but not CD4$^+$Foxp3$^-$ T cells, was significantly reduced by Compound A treatment. In addition, the ratio of CD8$^+$ T cells to Tregs was increased in Compound A-treated mice, although the frequency of CD8$^+$ T cells was not changed.

Figure 7A:
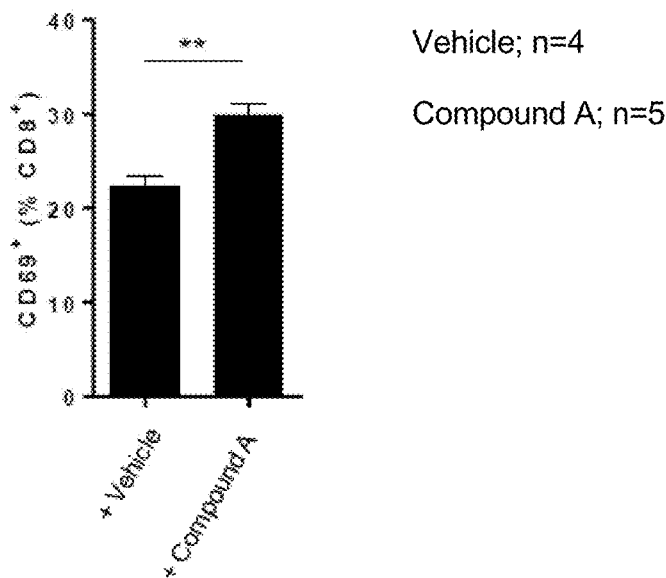

In FIG. 7A, the percentages of CD69$^+$ CD8$^+$ cells were analyzed by flow cytometry (*p<0.05, **p<0.01).

Figure 7B:
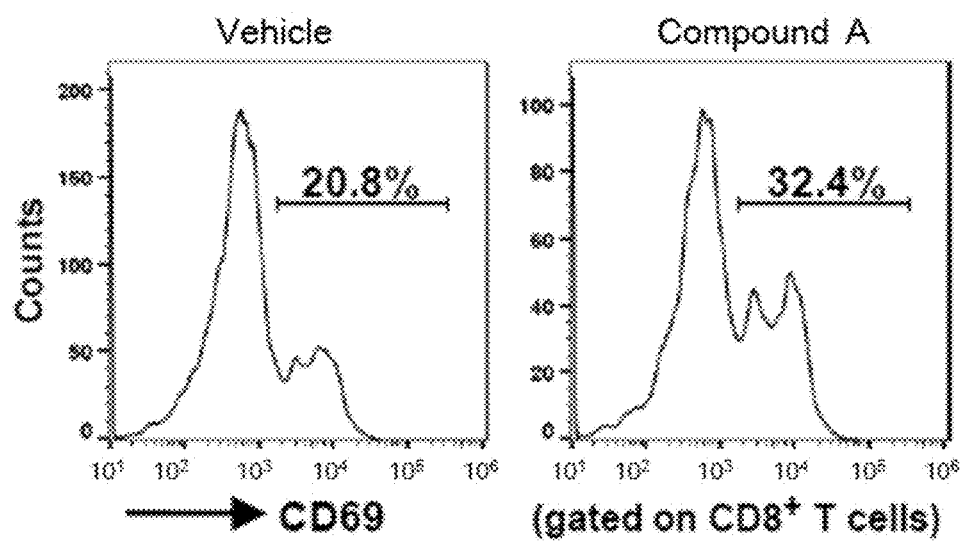

FIG. 7B depicts histograms of CD69 expression on CD8$^+$ T cells of livers from vehicle-treated mice (left side) and Compound A-treated mice (right side). The numbers in histograms indicate the percentages of CD69$^+$ cells.

The number of CD8$^+$ T cells expressing the activation marker CD69 was significantly increased in livers from Compound A-treated mice. This result indicates that the treatment of Compound A activates the functions of CD8$^+$ T cells in the tumor tissue.

Figure 8A:
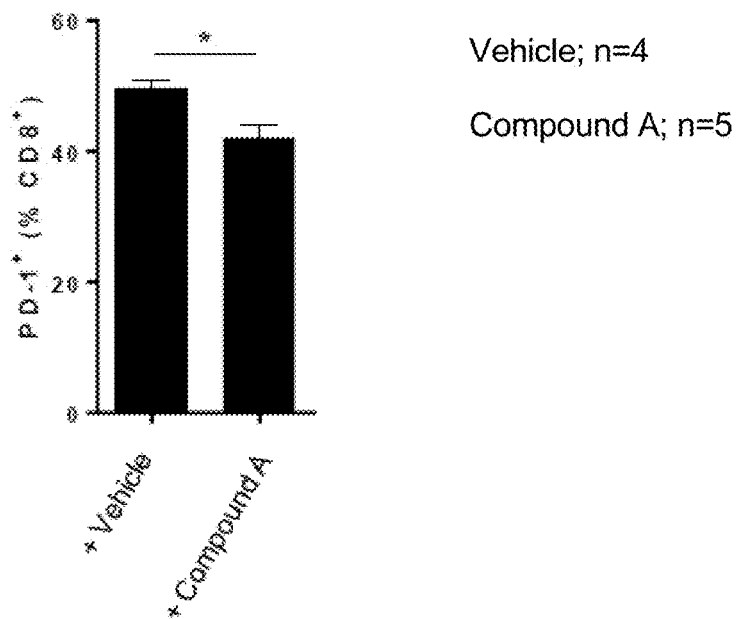

In FIG. 8A, the percentages of PD-1$^+$ CD8$^+$ cells were analyzed by flow cytometry (*p<0.05, **p<0.01).

Figure 8B:
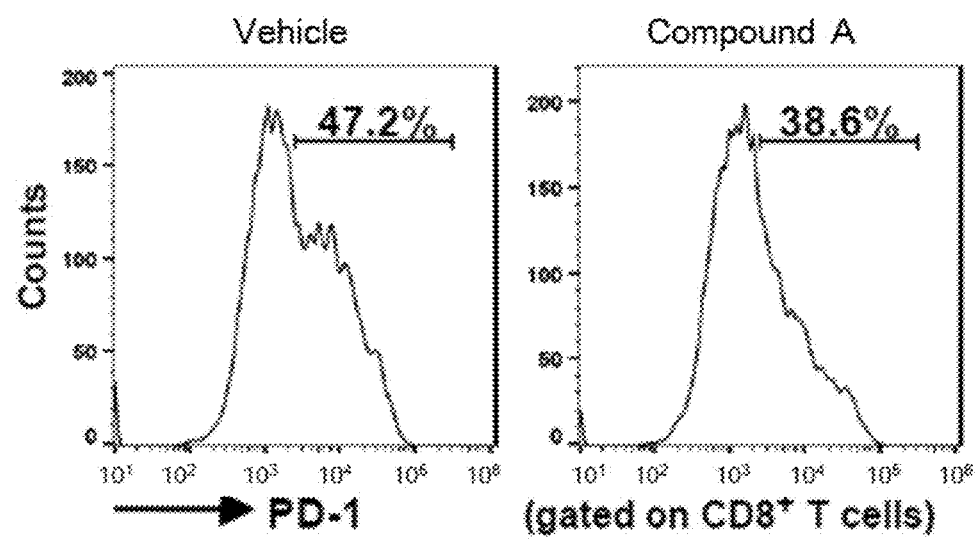

FIG. 8B depicts histograms of PD-1 expression on CD8$^+$ T cells of livers from vehicle-treated mice (left side) and Compound A-treated mice (right side). The numbers in the histograms indicate the percentages of PD-1$^+$ cells.

Administration of Compound A significantly reduced the number of CD8+ T cells expressing programmed cell death-1 (PD-1), a key inhibitory receptor on T cells in the tumor microenvironment.

DETAILED DESCRIPTION OF THE INVENTION

The compounds of the invention which are useful for the treatment of NASH-associated liver cancer are:
4-[(1S)-1-({[5-chloro-2-(3-fluorophenoxy)pyridin-3-yl]carbonyl}amino)ethyl]-benzoic acid (Compound A),
4-((1S)-1-{[5-chloro-2-(4-fluorophenoxy)benzoyl]amino}ethyl)benzoic acid (Compound B), and
3-[2-(4-{2-ethyl-4,6-dimethyl-1H-imidazo[4,5-c]pyridin-1-yl}phenyl)ethyl]-1-[(4-methylbenzene)sulfonyl]urea (Compound C),
or a pharmaceutically acceptable salt thereof.

The compounds of the invention also include the solvates, complexes, polymorphs, prodrugs, isomers, and isotope-labeled compounds thereof.

The compounds of the invention are disclosed in WO 2005/021508.

Pharmaceutically acceptable salts include the acid addition and base salts thereof. Suitable acid addition salts are formed from acids which form non-toxic salts. Examples include the acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Suitable base salts are formed from bases which form non-toxic salts. Examples include the aluminum, arginine, benzathine, calcium, choline, diethylamine, diolamine, glycine, lysine, magnesium, meglumine, olamine, potassium, sodium, tromethamine and zinc salts.

For a review on suitable salts, see "Handbook of Pharmaceutical Salts: Properties, Selection, and Use" by Stahl and Wermuth (Wiley-VCH, Weinheim, Germany, 2002).

A pharmaceutically acceptable salt of the compounds of the invention may be readily prepared by mixing solutions of the compound of the present invention and the desired acid or base as appropriate. The salt may precipitate from solution and be collected by filtration or may be recovered by evaporation of the solvent. The degree of ionization in the salt may vary from completely ionized to almost non-ionized.

The compounds of the invention may exist in both unsolvated and solvated forms. The term "solvate" is used herein to describe a molecular complex comprising the compound of the invention and one or more pharmaceutically acceptable solvent molecules, for example, ethanol.

Included within the scope of the invention are complexes such as clathrates, drug-host inclusion complexes wherein, in contrast to the aforementioned solvates, the drug and host are present in stoichiometric or non-stoichiometric amounts. Also included are complexes of the compounds containing two or more organic and/or inorganic components which may be in stoichiometric or non-stoichiometric amounts. The resulting complexes may be ionized, partially ionized, or non-ionized. For a review of such complexes, see J. Pharm. Sci., 64(8):1269-1288 by Haleblian (August 1975).

Hereinafter, all references to the compounds of the invention include references to salts, solvates and complexes thereof and to solvates and complexes of salts thereof.

The compounds of the invention include compounds of the invention as hereinbefore defined, polymorphs, prodrugs, and isomers thereof (including optical, geometric and tautomeric isomers) as hereinafter defined and isotopically-labeled compounds of the invention.

As stated above, the invention includes all polymorphs of the compounds of the invention as defined herein.

Also within the scope of the invention includes so-called "prodrugs" of the compounds of the invention. Thus, certain derivatives of the compounds of the invention which may have little or no pharmacological activity themselves can, when administered into or onto the body, be converted into the compounds having the formula of any one of the compounds of the invention having the desired activity, for example, by hydrolytic cleavage. Such derivatives are referred to as "prodrugs". Further information on the use of prodrugs may be found in "Pro-drugs as Novel Delivery Systems", Vol. 14, ACS Symposium Series (T. Higuchi and W. Stella) and "Bioreversible Carriers in Drug Design", Pergamon Press, 1987 (ed. E. B. Roche, American Pharmaceutical Association).

Prodrugs in accordance with the invention can, for example, be produced by replacing appropriate functionalities present in the compounds of the invention with certain moieties known to those skilled in the art as "pro-moieties" as described, for example, in "Design of Prodrugs" by H Bundgaard (Elsevier, 1985).

Some examples of prodrugs in accordance with the invention include:

(i) where the compound of the invention contains a carboxylic acid functionality (—COOH), an ester thereof, for example, replacement of the hydrogen with $(C_1-C_8)$alkyl;

(ii) where the compound of the invention contains an alcohol functionality (—OH), an ether thereof, for example, replacement of the hydrogen with $(C_1-C_6)$alkanoyloxymethyl; and (iii) where the compound of the invention contains a primary or secondary amino functionality (—NH$_2$ or —NHR where R≠H), an amide thereof, for example, replacement of one or both hydrogens with $(C_1-C_{10})$alkanoyl.

Further examples of substituent groups other than the foregoing examples are known to those skilled in the art and can be found in the aforementioned references, but not limited to them.

Finally, the compounds of the invention may themselves also act as prodrugs of other compounds of the invention.

Compounds of the invention containing one or more asymmetric carbon atoms can exist as two or more stereoisomers. Where a compound of the invention contains an alkenyl or alkenylene group, geometric cis/trans (or Z/E) isomers are possible. Where the compound contains, for example, a keto or oxime group or an aromatic moiety, tautomeric isomerism ("tautomerism") can occur. It follows that a single compound may exhibit more than one type of isomerism.

Included within the scope of the invention are all stereoisomers, geometric isomers and tautomeric forms of the compounds of the invention, including compounds exhibiting more than two types of equal isomerism, and mixtures of one or more thereof. Also included are acid addition or base salts wherein the counter ion is optically active, for example, D-lactate or L-lysine, or racemic, for example, DL-tartrate or DL-arginine.

Cis/trans isomers may be separated by conventional techniques well known to those skilled in the art, for example, chromatography and fractional crystallization.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of the invention contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50 (w/w) % isopropanol, typically from 2 to 20 (w/w) %, and from 0 to 5 (w/w) % of an alkylamine, typically 0.1 (w/w) % diethylamine. Concentration of the eluate affords the enriched mixture.

Stereoisomeric conglomerates may be separated by conventional techniques known to those skilled in the art (see, for example, Stereochemistry of Organic Compounds by E L Eliel (Wiley, New York, 1994)).

The invention includes all pharmaceutically acceptable isotopically-labelled compounds of the invention wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulfur, such as $^{35}$S.

Certain isotopically-labelled compounds of the invention, for example, those incorporating a radioactive isotope, are useful in drug and/or substrate tissue distribution studies associated with cancer therapy which includes diagnosis, alleviation of symptoms, improvement of QOL, and prophylaxis. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labelled compounds of the invention can generally be prepared by conventional techniques known to those skilled in the art or by processes analogous to those described in the accompanying Examples and Preparations using an appropriate isotopically-labeled reagents in place of the non-labeled reagent previously employed.

Pharmaceutically acceptable solvates in accordance with the invention include those wherein the solvent of crystallization may be isotopically substituted, e.g. $D_2O$, $d_6$-acetone, $d_6$-DMSO.

Compounds of the invention intended for pharmaceutical use may be administered as crystalline or amorphous products. They may be obtained, for example, as solid plugs, powders, or films by methods such as precipitation, crystallization, freeze drying, or spray drying, or evaporative drying. Microwave or radio frequency drying may be used for this purpose.

Each one of the compounds of the invention (i.e., Compound A, B or C) may be administered alone or in combination or in combination with one or more other drugs (or as any combination thereof). Generally, they will be administered as a formulation in association with one or more pharmaceutically acceptable additives. The term "additive" is used herein to describe any ingredient other than the compounds of the invention. The choice of additive will to a large extent depend on various factors, such as, the particular mode of administration, the effect of the additive on solubility and stability, and the nature of the dosage form. The compounds of the invention may be administered alone or in combination with a pharmaceutically acceptable carrier or diluent by either of the above routes previously indicated, and such administration can be carried out in single or multiple doses. More particularly, the compounds of the invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the compounds of the invention are present in such dosage forms at concentration levels ranging from 5% to 95% by weight. For oral administration, tablets containing various excipients such as microcrystalline cellulose, sodium citrate, calcium carbonate, dipotassium phosphate and glycine may be employed along with various disintegrants such as starch and preferably corn, potato or tapioca starch, alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

Thus, the invention provides the compounds of the invention, a solvate thereof, a prodrug thereof, a combination thereof, and a combination with one or more other pharmacologically active agents. In addition, the invention provides a pharmaceutical composition comprising the compounds of the invention and a pharmaceutically acceptable additive, a diluent, or a carrier, particularly for the treatment of NASH-associated liver cancer. Also, the invention provides a kit comprising: a first pharmaceutical composition comprising the compounds of the invention, or a pharmaceutically acceptable salt thereof; a second pharmaceutical composition; and a container.

A kit for the treatment of NASH-associated liver cancer, which includes the compounds of the invention, or the pharmaceutically acceptable salts thereof, is also one of the inventions. A commercial package comprising the pharmaceutical composition comprising the compounds of the invention, or the pharmaceutically acceptable salts thereof and a written matter associated therewith, wherein the written matter states that the compounds can or should be used for treating NASH-associated liver cancer is also one of the inventions.

Other features and advantages of the invention may be apparent from the following detailed description and the claims. Although particular embodiments of the invention have been described, various other known or usual changes and modifications in this field fall into the invention and are within the claims. The invention also includes the equivalents, changes, uses, or variations, which are within the spirit of the invention.

The compounds of the invention are administered in an amount effective to shrink cancer, reduce cancer tumor size, reduce cancer metastasis, regulate immune cell functions, and/or enhance effectiveness of cancer therapy. Such therapeutic effective amount varies in accordance with the specific compound of the invention, the specific condition to be treated, the patient's condition, the route of administration, the formulation, the field decision, and other factors. In the light of the disclosure, depending on the things known to those skilled in the art, it is decided by routine optimization techniques. The compounds of the invention can be administered via either the oral, parenteral or topical routes to mammals. In general, these compounds are most desirably administered to humans in doses ranging from 1 mg to 1000 mg, preferably from 10 mg to 600 mg, which may be administered in a single dose or in divided doses throughout the day, although variations will necessarily occur depending upon the weight and condition of the subject being treated, the disease state being treated and the particular route of administration chosen.

A pharmaceutical composition can include the compounds of the invention or a pharmaceutical salt thereof combined with a pharmaceutically acceptable transport medium or carrier.

As used herein the term "pharmaceutically acceptable transport medium" includes solvents, dispersion media, coatings, antibacterial and antifungal agents, isotonic and absorption delaying agents, and the like, compatible with pharmaceutical administration. The above medium also includes other active or inactive ingredients and is targeted to cancer tissues based on the composition.

Therapeutic efficacy of the compounds of the invention can be determined in light of this disclosure by standard therapeutic procedures in cell cultures or experimental animals, e.g., for determining the $ED_{50}$ (the dose therapeutically effective in 50% of the population).

The data obtained from the cell culture assays and animal studies can be used in formulating a range of dosage for use in humans. The dosage may vary depending upon the formulation and the route of administration. For any EP4 receptor antagonist used in the method of the invention (i.e., Compound A, B or C), the therapeutically effective dose can be estimated initially from cell culture assays. A dose may be formulated in animal models to achieve a circulating plasma concentration range that includes the $IC_{50}$ as determined in cell culture. Such information can be used to more accurately determine useful doses in humans or animals. Levels in plasma may be measured, for example, by high performance liquid chromatography.

It is well known to those skilled in the art that certain factors may influence the dosage and timing required to effectively treat a mammal including, but not limited to, the severity of the disease or disorder, previous treatments, the general health and/or age of the mammal, and other diseases present. Further, treatment of a mammal with a therapeutically effective amount of the compounds of the invention may include, but are not limited to, a single treatment, alternate-day treatment, or a series of treatments. The compounds of the invention can be administered via either the oral, parenteral or topical routes to mammals. In general, these compounds are most desirably administered to humans, for example, once a day, or in two to four divided portions a day.

The precise amount of the compounds administered to a human patient, will be particularly the responsibility of the attendant physician. However, the dose employed will depend upon a number of factors including the age and sex of the patient, the precise condition being treated and its severity, and the route of administration. In the case of oral administration, for example, a daily dosage in terms of the compounds of the invention is usually in the order of about 0.02 to 200 mg, and preferably about 0.1 to 100 mg, per 1 kg body weight of a mammal (including a human), which may be administered once a day or in two to four divided portions a day. More particularly, for example, administration to humans, is about 0.02 to 20 mg, per kg body weight, per day, more particularly, about 0.2 to 12 mg, per kg body weight, per day. Administration to dogs, for example, is about 0.5 to 25 mg, per kg body weight, per day, more particularly, about 1 to 10 mg, per kg body weight, per day. Administration to mice, for example, is about 1 to 100 mg, per kg body weight, per day, more particularly, about 3 to 30 mg, per kg body weight, per day.

The compounds of the invention are conveniently administered in the form of a pharmaceutical composition for treatment of NASH-associated liver cancer. Such composition may conveniently be presented for use in conventional manner in admixture with one or more pharmaceutically acceptable carriers or excipients.

While it is possible for the compounds of the invention to be administered as the raw chemical, it is preferable to present it as a pharmaceutical composition in the form of a pharmaceutical formulation. The formulations comprise the compounds together with one or more acceptable carriers or diluents, and optionally other therapeutic ingredients. The carrier(s) must be "acceptable" in the sense of being compatible with the other ingredients of the formulation and not deleterious to the recipient thereof.

A pharmaceutical composition is formulated to meet the desirable route of administration. The administration route is, for example, parenteral (e.g., intravenous, in the skin, subcutaneous), oral (e.g., ingestion or inhalation), percutaneous (local), mucosal, and rectum, and local (including percutaneous, oral, and sublingual) administration. A pharmaceutical composition formulated in the form of a solution or suspension can be prepared by the method described in, for example, Remington's Pharmaceutical Sciences, $18^{th}$ ed., Gennaro, ed., Mack Publishing Co., Easton, Pa., (1990).

The most suitable route of administration may be different depending upon, for example, the condition and disorder of the patient receiving the treatment. The formulations may conveniently be presented in unit dosage form and may be prepared by any of the methods well known in the art of pharmacy. All methods include the step of bringing into association the compound (i.e., the "active ingredient") with the carrier which constitutes one or more accessory ingredients. In general the formulations are prepared by uniformly and intimately bringing into association the active ingredient with a liquid carrier or a finely divided solid carrier or both and then, if necessary, shaping the product into the desired formulation.

Formulations of the present invention suitable for oral administration may be presented as discrete units, such as capsules, cachets or tablets (e.g., chewable tablets in particular for pediatric administration) each containing a predetermined amount of the active ingredient; as a powder or granule; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form, such as a powder or granule, optionally mixed with a binder, lubricant, inert diluent, lubricating, surface active or dispersing agent. Molded tablets may be made by molding in a suitable machine a mixture of the powdered active ingredient moistened with an inert liquid diluent. The tablets may optionally be coated or scored and may be formulated so as to provide slow or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampoules and vials, and may be stored in a freeze-dried (lyophilized) condition requiring only the addition of a sterile liquid carrier, for example, water-for-injection, immediately prior to use. Extemporaneous injection solutions and suspensions may be prepared from sterile powders, granules and tablets of the kind previously described.

Formulations for rectal administration may be presented as a suppository with the usual carriers such as cocoa butter, hard fat or polyethylene glycol.

Formulations for topical administration in the mouth, for example, buccally or sublingually, include lozenges comprising the active ingredient in a flavored basis such as sucrose and acacia or tragacanth, and pastilles comprising the active ingredient in a basis such as gelatin and glycerin or sucrose and acacia.

The compounds of the invention may also be formulated as depot preparations. Such long acting formulations may be administered by implantation (for example, subcutaneously or intramuscularly) or by intramuscular injection. Thus, for example, the compounds of the invention may be formulated with suitable polymeric or hydrophobic materials (for example, as an emulsion in an acceptable oil) or ion exchange resins, or as sparingly soluble derivatives, for example, as a sparingly soluble salt.

In addition to the ingredients particularly mentioned above, the formulations may include other agents conventional in the art having regard to the type of formulation in question, for example, those suitable for oral administration may include flavoring agents.

Second active agents that are small molecules can also be used to alleviate adverse effects associated with the administration of the compounds of the invention. However, like some large molecules, many are believed to be capable of providing a synergistic effect when administered with (e.g., before, after or simultaneously) the compounds of the invention. Examples of small molecule second active agents include, but are not limited to, anti-cancer agents, antibiotics, immunosuppressive agents, and steroids.

The invention also includes combining separate pharmaceutical compositions in kit form. The kit comprises two separate pharmaceutical compositions; a compound of the invention; and a second therapeutic agent as described herein. The kit comprises a container for containing the separate compositions, such as, a divided bottle or a divided foil packet, however, the separate compositions may also be contained within a single, undivided container. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

An example of such a kit is a so-called blister pack. Blister packs are well known in the packaging industry and are being widely used for the packaging of pharmaceutical unit dosage forms (tablets, capsules, and the like). Blister packs generally contain a sheet of relatively stiff material covered with a foil of a preferably transparent plastic material. During the packaging process, recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably, the strength of the sheet is such that the tablets or capsules can be removed from the blister pack by manually applying pressure on the recesses whereby an opening is formed in the sheet at the place of the recess. The tablet or capsule can then be removed via said opening.

In certain embodiments, the methods provided herein comprise administering the compounds of the invention in combination with one or more second active agents, and/or in combination with radiation therapy or surgery. Examples of the second active agent include, for example, additional EP4 antagonists, immune checkpoint inhibitors, PD-1 inhibitors, PD-L1 inhibitors, CTLA4 inhibitors, adoptive immune cell therapies, cancer vaccines, and other immuno-oncological drugs targeting, for example, colony-stimulating factor 1 receptor (CSF1R), indoleamine 2,3-dioxytenase (IDO), or carcinoembryonic antigen (CEA). Moreover, molecular-targeted anti-cancer drugs, and cancer chemotherapeutics are also included as the second active agent. More paticuraly, the second active agents include, for example, PD-1 antibodies such as nivolumab, labrolizumab/pembrolizumab, REGE2810, PD-L1 antibodies such as abelumab, atezolizumab, durvalumab, pembrolizumab, CTLA-4 antibodies such as ipilimumab and tremelimumab, molecular-targeted drugs such as anti-HER2 antibody, anti-VEGF antibody, anti-EGFR antibody, tyrosine kinase inhibitors against EGFR receptor, PDGFR receptor, VEGFR receptor kinases, c-kit, and Bcr-Abl, and anti-tumor chemotherapeutics such as alkylating agents, antimetabolites, anti-tumor antibiotics, anti-infective drugs, microtubule inhibitors, hormonal therapeutics, platinum drugs, topoisomerase inhibitors, humor therapeutics such as aromatase inhibors, anti-estrogen drugs, anti-androgen drugs, progesterone, estradiol, LH-RH agonists, and immune therapies such as adoptive T-cell therapy, adoptive dendritic cell therapy, adoptive NK cell therapy and cancer vaccine therapy. The administration of the compounds of the invention and the second active agents to a patient can occur simultaneously or sequentially by the same or different routes of administration. The suitability of a particular route of administration employed for a particular active agent will depend on the active agent itself (e.g., whether it can be administered orally without decomposing prior to entering the blood stream) and the disease being treated. Recommended routes of administration for the second active agents are known to those of ordinary skill in the art. See, e.g., Physicians' Desk Reference.

Definitions of Terms

"EP4 antagonist" refers to a compound which inhibits or blocks the cellular signaling triggered by the interaction of PGE2 with the EP4 receptor. Examples of EP4 antagonists include, but are not limited to, ER-819762, MK-2894, MF 498, ONO-AE3-208, evatanepag, ONO-AE2-227, BGC201531, ONO-AE3-240, GW 627368 and AH23848, which are listed in the IUPHAR database as antagonists of the EP4 receptor. Compounds A, B and C, and pharmaceutically acceptable salts thereof (the compounds of the invention), are also examples of EP4 antagonists.

An "immune checkpoint inhibitor" refers to a type of drug that blocks certain proteins made by some types of immune cells, such as T cells, and some cancer cells. These proteins help keep immune responses in check and can keep T cells from killing cancer cells. When these proteins are blocked, the brakes on the immune system are released and T cells are able to kill cancer cells better. Examples of immune checkpoint inhibitors include, but are not limited to, PD-1 inhibitors, CTLA-4 inhibitors, LAG-3 inhibitors, TIM-3 inhibitors, BTLA inhibitors, PD-L1 inhibitors, PD-L2 inhibitors, B7-1 inhibitors, B7-2 inhibitors, galectin-9 inhibitors, and HVEM inhibitors. The immune checkpoint inhibitors may be small molecules, peptides, proteins such as an antibody, nucleic acids or the like.

"PD-1 inhibitor" refers to an antibody or other molecule which inhibits programmed death protein 1 (PD1) function. Exemplary inhibitors/antibodies include, but are not limited to, the antibodies set forth in U.S. Pat. Nos. 7,029,674, 7,488,802, 7,521,051, 8,008,449, 8,354,509, 8,617,546 and 8,709,417. Particular embodiments of the antibody include MDX-1106/nivolumab, BMS-936558, (Bristol-Myers Squibb), labrolizumab (Merck), MK-3475/pembrolizumab (KEYTRUDA®, Merck), AMP-224 (GSK), and CT-011 (Cure Tech).

"PD-L1 inhibitor" refers to an antibody or other molecule which inhibits programmed death ligand 1 (PDL1) function. Exemplary antibodies include, but are not limited to, the antibodies set forth in U.S. Pat. Nos. 8,217,149, 8,383,796, 8,552,154 and 8,617,546. In a particular embodiment, the antibody is MPDL3280A/RG7446 (Roche), BMS-936559 (BMS), MEDI4736 (AstraZeneca), and MSB0010718C (MerckSerono).

"CTLA4 inhibitor" refers to an antibody or other molecule which inhibits cytotoxic t-lymphocyte antigen 4 (CTLA4) function. Exemplary inhibitors/antibodies include, but are not limited to, antibodies that are CTLA4 antagonists or the CTLA4 antibodies set forth in U.S. Pat. Nos. 8,685, 394 and 8,709,417. Some embodiments of the antibody include MDX-010 (ipilimumab, Bristol-Myers Squibb) and CP-675,206 (tremelimumab, AstraZeneca). In a particular embodiment, the antibody is ipilimumab and tremelimumab.

"Treatment," "treat," and "treating" refer to alleviating, inhibiting and/or reversing the progress of a cancer in a subject in need thereof. The term "treating" is inclusive of any indicia of success in the treatment or amelioration of the cancer, including any objective or subjective parameter such as abatement; remission; diminishing of symptoms or making the injury, pathology or condition more tolerable to the subject; delaying or slowing in the rate of progression, etc. Measurement of the treatment or amelioration may be based on, e.g., the results of a physical examination, a pathological test and/or a diagnostic test as known in the art. Treating may also refer to reducing the incidence or onset of a cancer, or a recurrence thereof (such as a lengthening in time of remission), as compared to that which would occur in the absence of the measure taken. The term "treatment", as used herein, includes not only shrinking the tumor tissue but also alleviation of symptoms, improvement of quality of life (QOL), and prophylaxis (radiotherapy, postoperative prevention of recurrence, adjuvant chemotherapy and the like).

A "pharmaceutically effective amount" refers to an amount that is effective for treating a cancer as noted through clinical testing and evaluation, patient observation, and/or the like. An "effective amount" can further designate an amount that causes a detectable change in biological or chemical activity. The detectable changes may be detected and/or further quantified by one skilled in the art for the relevant mechanism or process. Moreover, an "effective amount" can designate an amount that maintains a desired physiological state, i.e., reduces or prevents significant decline and/or promotes improvement in the condition. An "effective amount" can further refer to a therapeutically effective amount.

As used herein, the term "a pharmaceutically acceptable salt" is consistent with the examples provided above and refers to a relatively nontoxic, inorganic or organic acid salt of a compound of the invention. These salts may be prepared in situ during the final isolation and purification of the compounds or by reacting the purified compound in its free form separately with a suitable organic or inorganic acid and isolating the salt thus formed. Representative acid salts include, but are not limited to, acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinafoate salts. In one embodiment, the pharmaceutically acceptable salt is a hydrochloride/chloride salt.

"Second active agent" is a low molecular weight drug or biologic which has pharmacologically effective activity, and it includes, but is not limited to, PGE2 signal inhibitors such as additional EP4 antagonists, microsomal prostaglandin E synthase (mPGES)-1 inhibitor, COX-2 inhibitors, NSAIDs, and immune checkpoint inhibitors, immune cell-targeted drugs, molecular-targeted anti-cancer drugs, alkylating agents, antimetabolites, anti-tumor antibiotics, anti-infective drugs, microtubule inhibitors, hormonal therapeutics, platinum drugs, topoisomerase inhibitors, molecular-targeted drugs, molecular-targeted cancer therapeutics, immune therapeutics and so on.

"Anti-tumor therapy" includes, but is not limited to, therapies with anti-tumor vaccine therapy, and adoptive immune cell therapy such as adoptive T-cell therapy, adoptive dendritic cell therapy, or adoptive NK cell therapy, and also includes, but is not limited to, cancer radiation therapy, and surgical operation therapy.

"Biologic" includes, but is not limited to, a pharmacologically active protein, such as interferon gamma, and interleukin 2, and a pharmacologically active peptide, nucleic acid, and polysaccharide.

"Molecular-targeted drugs" include, but are not limited to, an anti-HER2 antibody, an anti-VEGF antibody, an anti-EGFR antibody, a tyrosine kinase inhibitor against a EGFR receptor, PDGFR receptor, VEGFR receptor kinase, c-kit, and Bcr-Abl.

"Immune therapeutics" include, but are not limited to, immune-regulating drugs, adoptive immune cell therapies, anti-tumor vaccine therapies and so on.

"NASH" refers to a nonalcoholic steatohepatitis, a syndrome that develops in patients who are not alcoholic; it causes liver damage that is histologically indistinguishable from alcoholic hepatitis. It develops most often in patients with at least one of the following risk factors: obesity, dyslipidemia, and glucose intolerance. Pathogenesis is poorly understood but seems to be linked to insulin resistance (e.g., as in obesity or metabolic syndrome).

"NASH-associated liver cancer" refers to a cancer, including hepatocellular carcinoma (HCC), and other cancer(s) that occur at liver-related organs, such as, liver blood vessel or bile duct that are induced by and/or associated with NASH. NASH-associated liver cancer is different from the hepatocellular carcinoma which is induced by hepatitis B or C viruses in terms of the pathogenesis of the disease.

"Metastatic cancer" refers to a cancer in which cancerous cells from an organ or body part has spread (through "metastasis") to another, non-adjacent organ or body part. The cancer at the non-adjacent organ or body part ("secondary tumor" or "metastatic tumor") includes cancerous cells originating from the organ or body part from which the cancer or cancerous cells has spread. Sites in which the secondary tumor may occur include, but are not limited to, lymph nodes, the lungs, brain and/or bones.

The term "EP4 signal" or "EP4 signaling", as used herein, means elevation of cAMP and following signal transductions in association with agonistic stimulation of EP4 receptor.

EXAMPLES

Example 1

Compound A inhibited the growth of liver cancer in a high fat diet-induced NASH-associated mouse liver cancer model.

Animal Experiments

C57/BL6 mice were purchased from CLEA Japan Inc. The $Tlr2^{-/-}$ mice (C57/BL6) were purchased from Oriental Yeast Co. Ltd.

Histology and Immunofluorescence Analysis

Hematoxylin and eosin staining and immunofluorescence analysis were performed as previously described (Yoshimoto et al., Nature, 2013, 499:97-101).

Immune Cell Isolation

Immune cells were obtained from mouse livers and were subjected to measuring cytokine production and flow cytometric analysis.

Statistical Analysis

Data were analyzed by unpaired t-test with Welch correction (two-side) or Man-Whitney test (two-side). P values less than 0.05 were considered significant. "NS" indicates not significant.

Study Results

Figure 1:
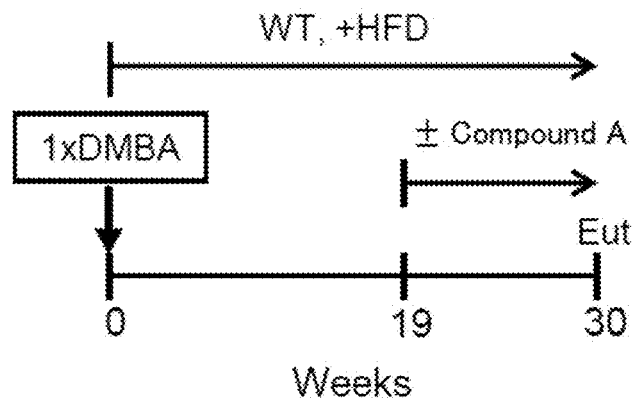
FIG. 1 depicts a mouse model timeline developed by treating with 7,12-dimethylbenz(a)anthracene ("DMBA"), and by feeding with a high fat diet (HFD). Compound A was administered to the mice every day from 19 weeks of age to 30 weeks of age and then euthanized ("Eut").
Figure 2:
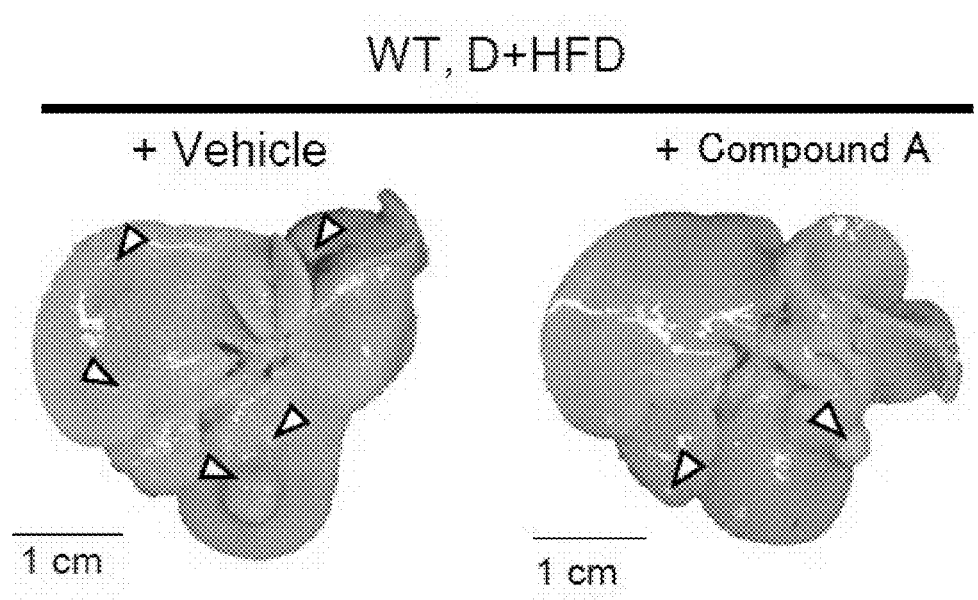
FIG. 2 is macroscopic photographs of the liver isolated from the vehicle-treated mice (left side) and Compound A-treated mice (right side). In this mouse model, the expression of EP4, but not other PGE2 receptors, was significantly upregulated in tumor tissues. Compound A or a vehicle (n=5, each) were treated to the mice every day from 19 weeks of age to 30 weeks of age. Arrowheads identify hepatocellular carcinomas (HCCs).
Figure 3:
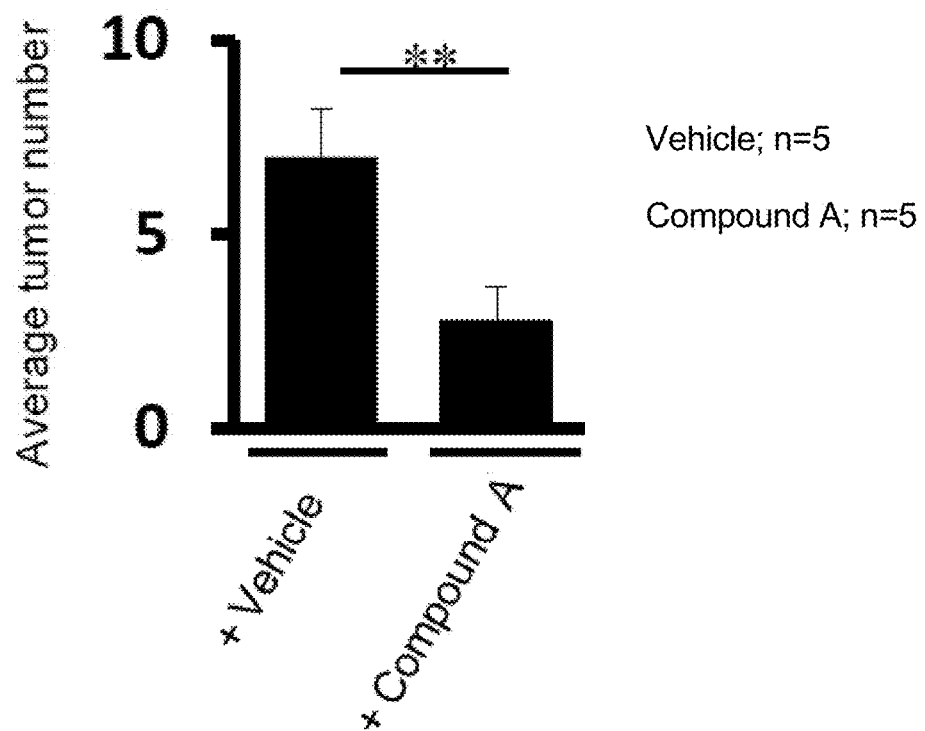
FIG. 3 depicts the average liver tumor numbers and the relative size distribution (classified as >6 mm, 2-6 mm, ≤2 mm). "NS" means not significant. Treatment with Compound A significantly inhibited the tumor number in the liver compared to the vehicle-treated mice. Tumor colony sized more than 6 mm completely disappeared after the Compound A therapy.
Figure 4:
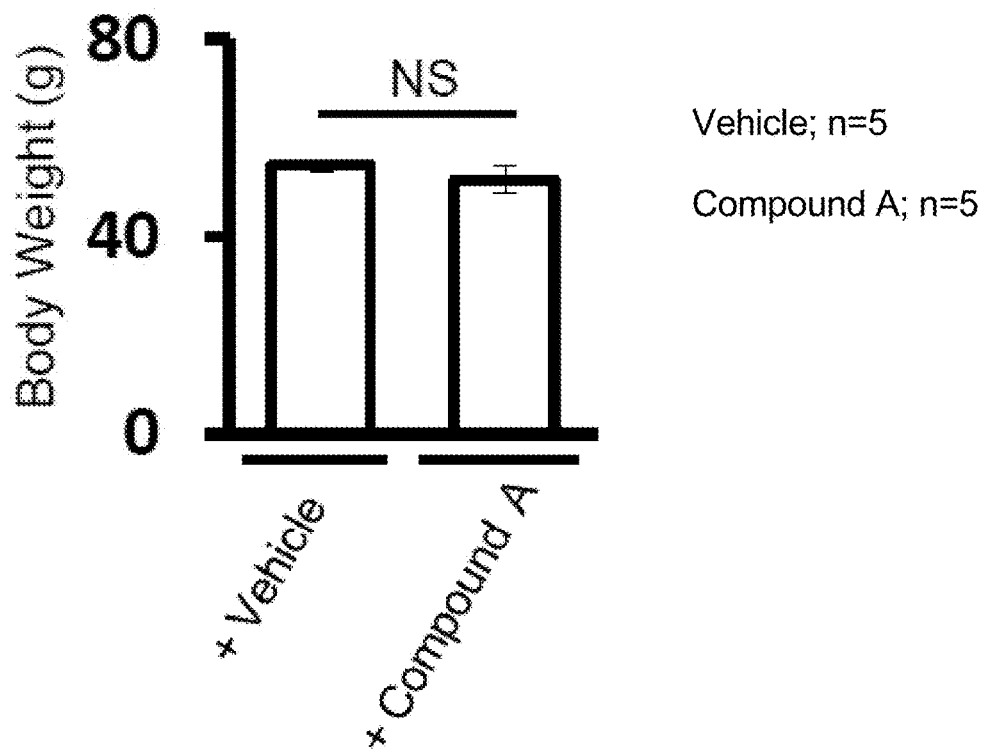
FIG. 4 depicts the average body weight of the vehicle-treated group and Compound A-treated group at the age of 30 weeks. Data are represented as means±SD. The daily treatment of Compound A did not affect the body weights of the mice. Therefore, Compound A demonstrated significant inhibition of liver cancer development without weight loss in the mice.

This mouse model was developed by treating with DMBA, 7,12-dimethylbenz(a)anthracene, and by feeding a high fat diet (HFD) (Ootani 2013). In this mouse model, the expression of EP4, but not other PGE2 receptors, was significantly upregulated in tumor tissues which suggests that EP4 could predominantly mediate PGE2 signaling in obesity-induced NASH-associated liver tumor tissue. In this experiment, Compound A 30 mg/kg QD was administered to the mice every day from 19 weeks of age to 30 weeks of age (FIG. 1). As a control, a separate group of mice were treated only with a vehicle and no active ingredient. Hepatocellular carcinoma (HCC) development in the Compound A-treated mice was strongly reduced as compared to the vehicle-treated mice (FIGS. 2 and 3). Notably, however, Compound A treatment did not influence body weight (FIG. 4).

Figure 5A:
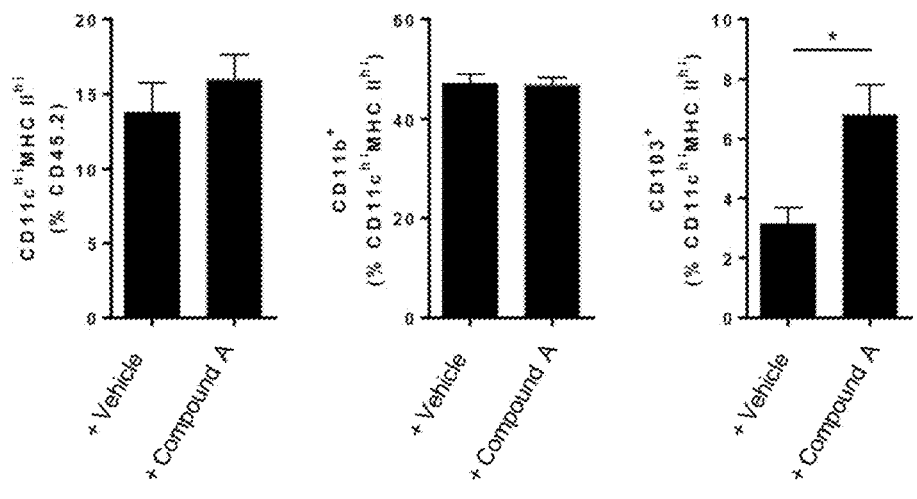
FIG. 5A depicts flow cytometry analysis of immune cells between vehicle-treated mice or Compound A-treated mice. The percentages of total CD11c$^{hi}$ MHC class II (MHC II)$^{hi}$, CD11b$^+$ CD11c$^{hi}$ MHC II$^{hi}$, or CD103$^+$ CD11c$^{hi}$ MHC II$^{hi}$ cells were analyzed by flow cytometry. Data are represented as means±SEM.
Figure 5B:
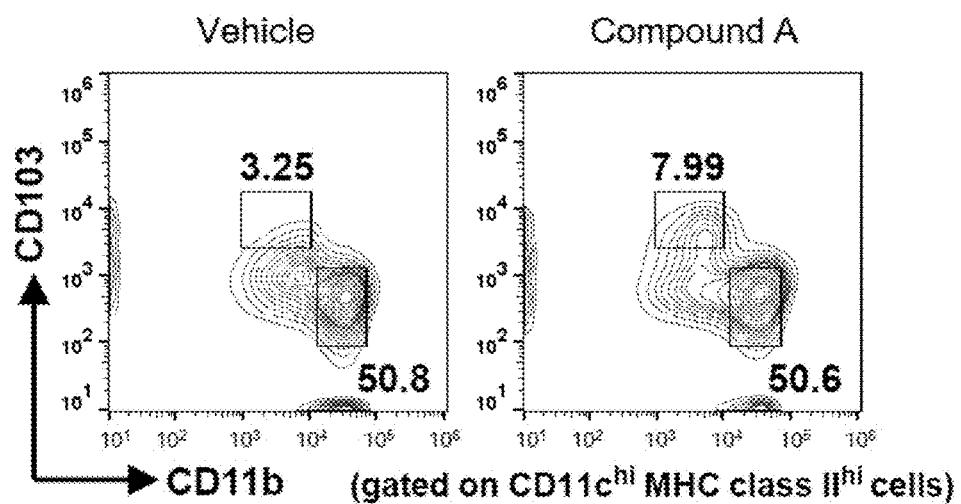
FIG. 5B depicts dot plots of CD11b and CD103 expression in CD11c$^{hi}$ MHC class II$^{hi}$ cell compartments of livers from vehicle-treated mice (left side) and Compound A-treated mice (right side). The numbers in the plots indicate the percentages of cells in the indicated gate.

The impact of EP4 blockage on the prevalence and activation status of immune cells was assessed. Although the frequencies of CD1 chi MHC class IIhi dendritic cells (DCs) and CD11 b+ DCs were not changed, the population of CD103+ DCs, which are essential for anticancer immune responses (Fuertes et al., J. Exp. Med., 2011, 208:2005-2016; Salmon et al., Immunity, 2016, 44:924-938; and Zelenay et al., Cell, 2015, 162:1257-1270), was increased in the Compound A-treated group (FIG. 5A and FIG. 5B). The frequency of $CD4^+Foxp3^+$ regulatory T cells (Tregs), but not $CD4^+Foxp3^-$ T cells, was significantly reduced by Compound A treatment (FIG. 6A and FIG. 6B). In addition, the ratio of $CD8^+$ T cells to Tregs was increased in Compound A-treated mice, although the frequency of $CD8^+$ T cells was not changed (FIG. 6A and FIG. 6B). Moreover, the number of $CD8^+$ T cells expressing the activation marker CD69 was significantly increased in livers from Compound A-treated mice (FIG. 7A and FIG. 7B). In contrast, administration of Compound A significantly reduced the number of $CD8^+$ T cells expressing programmed cell death-1 (PD-1), a key inhibitory receptor on T cells in the tumor microenvironment (FIG. 8A and FIG. 8B). These results suggest that blocking the EP4 pathway could re-activate antitumor immunity in the NASH-associated liver tumor microenvironment.

Conclusion

EP4 antagonist Compound A significantly inhibited the growth and development of an obesity-induced NASH-associated mouse liver cancer model. Compound A treatment to the mouse model increased frequencies of DC subtype which is essential for the anti-cancer immune response ($CD103^+$) and decreased the expression of PD-1 on cytotoxic $CD8^+$ T cells in tumor tissue. Compound A treatment also decreased the population of immune-suppressive Treg cells ($Foxp3^+$) in tumor tissues.

Example 2

Compound A in combination with a PD-1 antibody is expected to show a higher anti-tumor efficacy than Compound A alone in the HFD-induced NASH-associated mouse liver cancer model.

Study Methods

The same mouse model as Example 1 would be used to test the efficacy of Compound A in combination with a PD-1 antibody in HFD-induced NASH-associated mouse liver cancer model. Accordingly, Example 1 is repeated except a PD-1 antibody is also administered with Compound A in the Compound-A treated group.

Results

Compound A in combination with the PD-1 antibody therapy is expected to show higher anti-tumor efficacy than the Compound A-treated mice of Example 1 in the HFD-induced NASH-associated mouse liver cancer model.

Example 3

Compound B treatment is expected to inhibit the growth of liver cancer in the HFD-induced NASH-associated mouse liver cancer model.

Study Methods

The same mouse model as Example 1 would be used to test the efficacy of Compound B. Thus, Example 1 is repeated except Compound B is used instead of Compound A.

Study Results

Compound B therapy is expected to inhibit the growth of liver cancer in the HFD-induced NASH-associated mouse liver cancer model. Compound B is expected to control the immune cell function in tumor tissue in the same manner as Compound A in Example 1.

Conclusion

EP4 antagonist Compound B is expected to inhibit the growth and development in NASH-associated mouse liver cancer model consistent with the results of Compound A in Example 1. Compound B treatment to the mouse model is expected to increase frequencies of DC subtype which is essential for the anti-cancer immune response ($CD103^+$) and decrease the expression of PD-1 on cytotoxic $CD8^+$ T cells in tumor tissue. Compound B treatment is also expected to decrease the population of immune-suppressive Treg cells (Foxp3$^+$) in tumor tissues.

Example 4

Compound B in combination with a PD-1 antibody is expected to show a higher anti-tumor efficacy than Compound B alone in the HFD-induced NASH-associated mouse liver cancer model.
Study Methods
The same mouse model as Example 3 would be used to test the efficacy of Compound B in combination with a PD-1 antibody in HFD-induced NASH-associated mouse liver cancer model. Accordingly, Example 3 is repeated except a PD-1 antibody is also administered with Compound B in the Compound-B treated group.
Results
Compound B in combination with the PD-1 antibody therapy is expected to show a higher anti-tumor efficacy than the Compound B-treated mice of Example 3 in the HFD-induced NASH-associated mouse liver cancer model.

Example 5

Compound C treatment is expected to inhibit the growth of liver cancer in the HFD-induced NASH-associated mouse liver cancer model.
Study Methods
The same mouse model with Example 1 would be used to test the efficacy of Compound C. Accordingly, Example 1 is repeated except Compound C is used instead of Compound A.
Study Results
Compound C therapy is expected to inhibit the growth of liver cancer in the HFD-induced NASH-associated mouse liver cancer model. Compound C is expected to control the immune cell function in tumor tissue in the same manner as Compound A in Example 1.
Conclusion
EP4 antagonist Compound C is expected to inhibit the growth and development in NASH-associated mouse liver cancer model consistent with the results of Compound A in Example 1 and the expected results of Compound B in Example 3. Compound C treatment to the mouse model is expected to increase frequencies of DC subtype which is essential for the anti-cancer immune response (CD103$^+$) and decrease the expression of PD-1 on cytotoxic CD8$^+$ T cells in tumor tissue. Compound C treatment is also expected to decrease the population of immune-suppressive Treg cells (Foxp3$^+$) in tumor tissues.

Example 6

Compound C in combination with a PD-1 antibody is expected to show a higher anti-tumor efficacy than Compound C alone in the HFD-induced NASH-associated mouse liver cancer model.
Study Methods
The same mouse model as Example 5 would be used to test the efficacy of Compound C in combination with a PD-1 antibody in HFD-induced NASH-associated mouse liver cancer model. Accordingly, Example 5 is repeated except a PD-1 antibody is also administered with Compound C in the Compound-C treated group.
Results
Compound C in combination with the PD-1 antibody therapy is expected to show a higher anti-tumor efficacy than the Compound C-treated mice of Example 5 in the HFD-induced NASH-associated mouse liver cancer model.

The invention claimed is:

1. A method for the treatment of NASH-associated liver cancer which comprises administering a pharmaceutically effective amount of an EP4 antagonist to a human or an animal in need thereof,
    wherein the EP4 antagonist is at least one compound selected from the group consisting of:
    4-[(1S)-1-({[5-chloro-2-(3-fluorophenoxy)pyridin-3-yl]carbonyl}amino)ethyl]-benzoic acid (Compound A), and
    4-((1S)-1-{[5-chloro-2-(4-fluorophenoxy)benzoyl]amino}ethyl)benzoic acid (Compound B),
    or a pharmaceutically acceptable salt thereof.

2. The method of claim 1, further comprising administering the pharmaceutically effective amount of the EP4 antagonist in combination with a second active agent, an anti-tumor therapy or both.

3. The method of claim 2, wherein the second active agent is an immune checkpoint inhibitor.

4. The method of claim 2, wherein the second active agent is a PD-1 inhibitor.

5. The method of claim 1, wherein the EP4 antagonist is 4-[(1S)-1-({[5-chloro-2-(3-fluorophenoxy)pyridin-3-yl]carbonyl}amino)ethyl]-benzoic acid (Compound A), or a pharmaceutically acceptable salt thereof.

6. The method of claim 5, further comprising administering the pharmaceutically effective amount of the EP4 antagonist in combination with a second active agent, an anti-tumor therapy or both.

7. The method of claim 6, wherein the second active agent is an immune checkpoint inhibitor.

8. The method of claim 6, wherein the second active agent is a PD-1 inhibitor.

9. A method of therapy for the treatment of NASH-associated liver cancer in a human or an animal in need thereof, which results in at least one effect selected from the group consisting of:
    increasing DCs, mouse CD103$^+$ DC or a corresponding DC class in the human or the animal, which activates anti-tumor immune function in the human or the animal,
    decreasing Foxp3$^+$ Treg cells which suppress anti-tumor immune function in the human or the animal,
    increasing CD8$^+$/Treg population ratio in the human or the animal,
    increasing population of activated CD8$^+$ T cells in the human or the animal, and
    decreasing PD-1 expression in CD8$^+$ T cells in the human or the animal,
    wherein the method comprises administering a therapeutically effective amount of an EP4 antagonist to the human or the animal,
    wherein the EP4 antagonist is at least one compound selected from the group consisting of:
    4-[(1S)-1-({[5-chloro-2-(3-fluorophenoxy)pyridin-3-yl]carbonyl}amino)ethyl]-benzoic acid (Compound A), and
    4-((1S)-1-{[5-chloro-2-(4-fluorophenoxy)benzoyl]amino}ethyl)benzoic acid (Compound B),
    or a pharmaceutically acceptable salt thereof.

10. The method of claim 9, further comprising administering the pharmaceutically effective amount of the EP4 antagonist in combination with a second active agent, an anti-tumor therapy or both.

11. The method of claim 10, wherein the second active agent is an immune checkpoint inhibitor.

12. The method of claim 10, wherein the second active agent is a PD-1 inhibitor.

13. The method of claim 9, wherein the EP4 antagonist is 4-[(1S)-1-({[5-chloro-2-(3-fluorophenoxy)pyridin-3-yl]carbonyl}amino)ethyl]-benzoic acid (Compound A), or a pharmaceutically acceptable salt thereof.

14. The method of claim 13, further comprising administering the pharmaceutically effective amount of the EP4 antagonist in combination with a second active agent, an anti-tumor therapy or both.

15. The method of claim 14, wherein the second active agent is an immune checkpoint inhibitor.

16. The method of claim 14, wherein the second active agent is a PD-1 inhibitor.

17. The method of claim 1, wherein the EP4 antagonist is 4-((1S)-1-{[5-chloro-2-(4-fluorophenoxy)benzoyl]amino}ethyl)benzoic acid (Compound B), or a pharmaceutically acceptable salt thereof.

18. The method of claim 17, further comprising administering the pharmaceutically effective amount of the EP4 antagonist in combination with a second active agent, an anti-tumor therapy or both.

19. The method of claim 18, wherein the second active agent is an immune checkpoint inhibitor.

20. The method of claim 18, wherein the second active agent is a PD-1 inhibitor.

21. The method of claim 9, wherein the EP4 antagonist is 4-((1S)-1-{[5-chloro-2-(4-fluorophenoxy)benzoyl]amino}ethyl)benzoic acid (Compound B), or a pharmaceutically acceptable salt thereof.

22. The method of claim 21, further comprising administering the pharmaceutically effective amount of the EP4 antagonist in combination with a second active agent, an anti-tumor therapy or both.

23. The method of claim 22, wherein the second active agent is an immune checkpoint inhibitor.

24. The method of claim 22, wherein the second active agent is a PD-1 inhibitor.

* * * * *